United States Patent [19]

Serikov

[11] Patent Number: 5,658,560
[45] Date of Patent: Aug. 19, 1997

[54] METHOD OF TREATING ENDOTOXEMIA BY ADMINISTERING TYLOXAPOL

[76] Inventor: Vladimir B. Serikov, 51-51, 2nd Murinsky Ave. 194021, St. Petersburg, Russian Federation

[21] Appl. No.: 289,116

[22] Filed: Aug. 11, 1994

Related U.S. Application Data

[63] Continuation-in-part of Ser. No. 181,803, Jan. 18, 1994, abandoned.

[51] Int. Cl.$^6$ .................. A61K 31/765; A61K 31/77; A61K 38/00
[52] U.S. Cl. .................. 424/78.31; 514/2; 435/198
[58] Field of Search .................. 424/78.38, 78.31; 514/921, 885, 2, 4, 16, 21; 568/608, 622, 624; 549/429; 435/198

[56] References Cited

U.S. PATENT DOCUMENTS

| | | | |
|---|---|---|---|
| H1168 | 4/1993 | McKenna et al. | 514/28 |
| 3,450,502 | 6/1969 | Hymes. | |
| 3,577,522 | 5/1971 | Hymes. | |
| 3,740,421 | 6/1973 | Schmolka. | |
| 4,100,271 | 7/1978 | Krezanoski. | |
| 4,100,276 | 7/1978 | von Daehne et al.. | |
| 4,186,253 | 1/1980 | Yokoyama et al.. | |
| 4,395,393 | 7/1983 | Schmolka. | |
| 4,510,132 | 4/1985 | Vaara. | |
| 4,844,894 | 7/1989 | Ribi. | |
| 4,957,910 | 9/1990 | Sutton et al.. | |
| 5,004,757 | 4/1991 | Boucher | 514/694 |
| 5,034,383 | 7/1991 | Gaffar et al.. | |
| 5,071,649 | 12/1991 | Hunter | 424/78.38 |
| 5,080,894 | 1/1992 | Hunter et al. | 424/78.38 |
| 5,089,260 | 2/1992 | Hunter et al. | 424/78.38 |
| 5,114,708 | 5/1992 | Hunter et al. | 514/716 |
| 5,152,979 | 10/1992 | Hunter | 424/78.38 |
| 5,182,104 | 1/1993 | Marcus et al. | 424/78.07 |
| 5,183,687 | 2/1993 | Hunter | 424/78.34 |
| 5,190,748 | 3/1993 | Bachynsky et al. | 424/78.08 |
| 5,221,669 | 6/1993 | Anand et al. | 514/58 |
| 5,240,702 | 8/1993 | Hunter et al. | 424/78.31 |
| 5,264,356 | 11/1993 | Rohrschneider | 435/236 |

OTHER PUBLICATIONS

D. Attwood et al., Surfactant System, Chapman & Hall, (1983).

E.Y. Chi et al., "Freeze-fracture study of mast cell secretion", Proc. Natl. Acad. Sci., vol. 73, No. 8, pp.2823–2827, Aug. 1976.

F.V. Chisari et al., "Physiologic Concentrations of Normal Human Plasma Lipoproteins Inhibit the Immortalization of Peripheral B Lymphocytes by the Epstein-Barr Virus", J. Clin. Invest., vol. 68, pp.329–336, Aug. 1981.

J.A. Cook et al., "Modulation of Macrophage Arachidonic Acid Metabolism: Potential Role in the Susceptibility of Rats to Endotoxic Shock", Circulatory Shock, vol. 9, pp. 605–617, (1982).

E.B. Eichbaum et al., "Chlyomicrons Can Inhibit Endotoxin Activity in Vitro", J. of Surgical Research, vol. 51, pp.413–416, (1991).

K. Emancipator et al., "In Vitro Inactivation of Bacterial Endotoxin by Human Lipoproteins and Apolipoproteins", Infection and Immunity, vol. 60, No. 2, pp.596–601, Feb. 1992.

P.M. Flynn et al., "Polymyxin B Moderates Acidosis and Hypotension in Establish, Experimental Gram–Negative Septicemia", J. of Infectious Diseases, vol. 156, No. 5, pp.706–712, Nov. 1987.

M.F. Geertsma et al., "Ingestion of pulmonary surfactant by human monocytes inhibits their antibacterial functions", Mononuclear Phagocytes, Ch. 40, pp.308–314, (1992).

G. Gomez et al., "Protective Action of Luminal Bile Salts in Necrotizing Acute Pancreatitis in Mice", J. Clin. Invest., vol. 86, pp.323–331, Jul. 1990.

R.L. Goodman et al., "Perfluorocarbon Emulsions in Cancer Therapy: Preliminary Observations on Presently Available Formulations", Int. J. Radiation Oncology Biol. Phys., vol. 10, No. 8, pp. 1421–1424, Aug. 1984.

H.W. Harris et al., "Chylomicrons Alter the Fate of Endotoxin, Decreasing Tumor Necrosis Factor Release and Preventing Death", J. of Clinical Investigation, Inc., vol. 91, pp.1028–1034, Mar. 1993.

H.W. Harris et al., "Human Very Low Density Lipoproteins and Chylomicrons Can Protect against Endotoxin–induced Death in Mice", J. of Clinical Investigation, Inc., vol. 86, pp.696–702, Sep. 1990.

T. Ishikawa et al., "Changes in the concentration of plasma lipoproteins and apoproteins following the administration of Triton WR 1339 to rats", J. of Lipid Research, vol. 20, pp.254–264, (1979).

T. Kobayashi et al., "Vesiculation of Platelet Plasma Membranes Induced by Synthetic Phosphatidylcholines", J. Pharmacobio–Dyn., vol. 9, s–131, (1986).

M. Koike et al., "Electron Microscopic Studies on Mode of Action of Polymyxin", J. of Bacteriology, vol. 97, No. 1, pp.448–452, Jan. 1969.

T.A. Lane et al., "Paralysis of Phagocyte Migration Due to an ARtificial Blood Substitute", Blood, vol. 64, No. 2, pp.400–405, Aug. 1984.

R.C. Lee et al., "Surfactant–induced sealing of electropermeablized skeletal muscle membranes in vivo", Proc. Natl. Acad. Sci., vol. 89, pp.4524–4528, May 1992.

D.F. Nutting et al., "Hypolipidemic Effect of Intravenous Pluronic L–81 in Fasted Rats Treated with Triton WR–1339: Possible Inhibition of Hepatic Lipoprotein Secretion", Horm. metabol. Res., vol. 21, pp.113–115, (1989).

R.T. Proffiti et al., "Liposomal Blockade of the Reticuloendothelial System: Improved Tumor Imaging with Small Unilamellar Vesicles", Science, vol. 220, pp.502–505, Apr. 29, 1983.

(List continued on next page.)

Primary Examiner—Marian C. Knode
Assistant Examiner—Sheela J. Huff

[57] ABSTRACT

A method of treatment of toxemia in bacterial infection by administration of a pharmaceutical composition comprising a non-ionic biologically active detergent is provided.

2 Claims, 1 Drawing Sheet

OTHER PUBLICATIONS

V.B. Serikov et al., "Formation of Microvesicles in the Endothelial Cells. Parameters of Microvesicle Evolution", *Biol. Membranology*, vol. 4, pp. 947–954, (1987).

J. Sernatinger et al., "Neutralization of Mouse Xenotropic Virus by Lipoproteins Involves Binding to the Virions", *J. gen. Virol.*, vol. 69, pp.2657–2661, (1988).

D.C. Stokes et al., "Polymyxin B Prevents Lipopolysaccharide-Induced Release of Tumor Necrosis Factor–$\alpha$ from Alveolar Macrophages", *J. of Infectious Diseases*, vol. 160, No. 1, pp.52–57, Jul. 1989.

D.R. Storm et al., "Polymyxin and Related Peptide Antibiotics", *Ann. Rev. Biochem.*, vol. 46, pp.723–763, (1977).

M.J. Thomassen et al., "Synthetic Surfactant (Exosurf) Inhibits Endotoxin–stimulated Cytokine Secretion by Human Alveolar Macrophages", *Am. J. Respir. Cell Mol. Biol.*, vol. 7, pp.257–260, (1992).

J.H. Williams, Jr. et al., "Modulation of Rat Granulocyte Traffic by a Surface Active Agent in Vitro and Bleomycin Injury", *Proc. of the Society for Experimental Biology and Medicine*, vol. 188, pp.461–470, (1988).

V. Wunderlich et al., "Lytic Action of Neurotropic Drugs on Retroviruses in Vitro", *Euro. J. Cancer*, vol. 16, pp. 1127–1132, (1980).

C.J. van Oss et al., Phagocytic Engulfment and Cell Adhesiveness, M. Dekker, Inc., NY, (1975).

Endothelial Cell Vesicles, Progress in Applied Microcirculation, vol. 9, Ed. F. Hammersen, S. Karger, Basel, (1985).

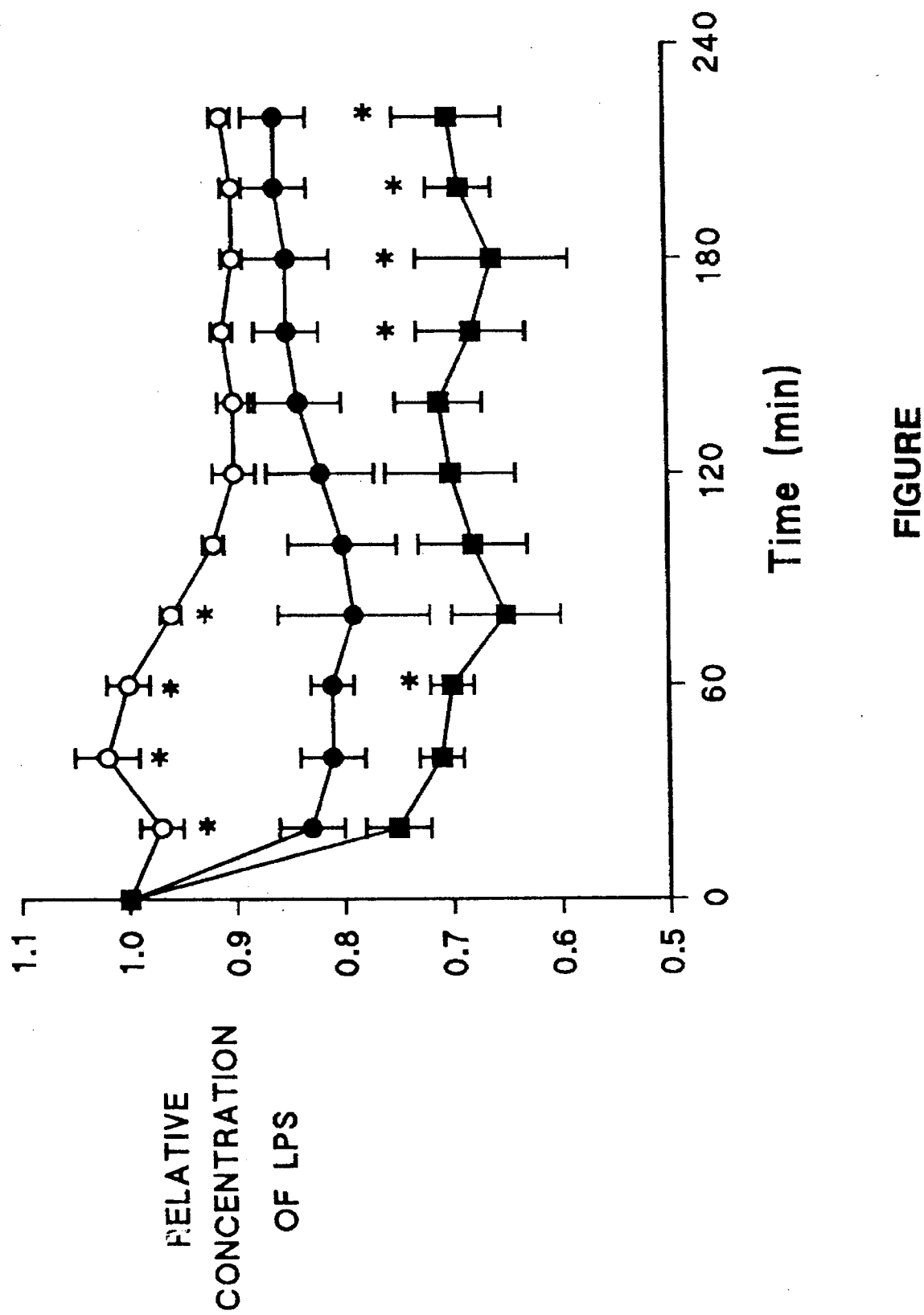
FIGURE

METHOD OF TREATING ENDOTOXEMIA BY ADMINISTERING TYLOXAPOL

CROSS-REFERENCE TO RELATED APPLICATIONS

This application is a continuation-in-part of U.S. patent application Ser. No. 08/181,803, filed Jan. 18, 1994 now abandoned.

FIELD OF THE INVENTION

This invention relates to methods of treatment of toxemia in bacterial infection.

BACKGROUND OF THE INVENTION

The plasma membrane of eukaryotic cells serves as a barrier against invading toxins, including certain bacteria. Endocytosis is the main transfer pathway of such items into immune system, barrier endothelial, and epithelial cells. Morphologically, endocytosis occurs by the formation of an invagination in the cell membrane, transformation of the invagination into a vesicle or continuous irregular channel, and its motion towards the other side or inside the cell. All nucleated interphase cells express continuous, high-capacity endocytotic activity wherein components of the cell medium are internalized in membrane-bound vesicles.

Receptor mediated endocytosis occurs primarily through clatrin-coated vesicles approximately 100 nanometers (nm) in diameter which form by the invagination of specialized coated-pit domains of the plasma membrane. Coated vesicles achieve efficient uptake of toxins, viruses, nutrient carriers, growth factors, peptide hormones, antigens, and other physiological ligands that bind to specific receptors expressed on the cell surface (see Cell, 32:663–667, 1983). In addition, solutes and particles are internalized nonspecifically in the fluid media of the vesicles by the process of fluid-phase endocytosis (see J. Cell Biol., 96:1–27, 1983).

The cells of the immune system are responsible for host reaction to the invasion of foreign materials into the body. Prevention and elimination of bacterial infection is a primary function of immune system cells, which is accomplished in part by endocytotic activity.

A particularly severe form of bacterial infection is sepsis, the generalized occupation of the body by bacteria. Sepsis and associated endotoxemia are among the most important pathologic situations where an unsatisfactory response of the immune system may lead to death. Presently, Gram-negative septicemia is among the leading causes of death in hospitals, despite potent antibiotics and vasoactive drugs. The fatality due to septicemia has remained 30 to 50% in the last decade.

Experimental evidence in both humans and animals has shown that many of the features of Gram-negative septicemia are due to endotoxin (see New Eng. J. Med., 307:1225–1230, 1982). Endotoxin is a lipopolysaccharide (LPS) present in the cell wall of certain bacterial species, including Gram-negative bacteria. The LPS molecule consists of a polysaccharide region covalently bound to a lipid region, termed lipid A. The lipid A molecules mediate most of the biological effects of endotoxins (see Am. J. Pathol., 93:527–617, 1978). Normal biological barriers are efficient to prevent endotoxin entry. In humans the gut contains large amounts of Gram-negative bacteria, that continuously project endotoxin. This endotoxin may transport across gut mucosa and then be removed by Kupffer cells of the liver (see Hepatology, 1:458–465, 1981).

Endotoxin induces many deleterious biological reactions in humans including fever, hypotension, shock and disseminated intravascular coagulation (see Ann. Rev. Med., 38:417–432, 1987). Endotoxin activates the coagulation, fibrinolytic and complement system (see Mol. Immunol., 24:319–332, 1987). Endotoxin also stimulates the arachidonic acid system, and activates polymorphonuclear cells, leukocytes and macrophages (see J. Clin. Invest., 77:1233–1243, 1986).

After contact with endotoxin, macrophages release special peptides, called cytokines. Among them are a few of a major importance: Interleukin-1 and Tumor Necrosis Factor (TNF) (see The Lancet, I:1122–1126, 1989). Cytokines modulate the development of alterations in cell function. All organs are the targets for endotoxin action in septicemia, however the lungs, liver and kidney are in particular damaged in sepsis, which leads to the development of respiratory, liver and kidney failure. Endotoxin induces cardiovascular disfunction and shock, which together lead to death.

Bacterial infection in sepsis is a subject to antibiotic therapy. However, the main unresolved problem in sepsis treatment remains endotoxemia, which requires, first of all, scavenging and inactivation of LPS. Attempts at treatment using monoclonal antibodies against LPS or LPS-binding protein have not proven an effective mode of therapy (see Discover, Nov:115–119, 1993). However, there are natural scavengers of LPS: The lipoproteins.

Endotoxemia is accompanied by alterations in lipid metabolism. Hyperlipidemia occurs in endotoxin-treated animals (see Am. J. Physiol., 253:E59–64, 1987), as well as during Gram-negative bacterial infection (see Clin. Chem., 32:142–145, 1986). In endotoxin-induced hyperlipidemia, a increased concentration of plasma triglycerides, very-low density lipoproteins (VLDL), low-density lipoproteins (LDL) and high-density lipoproteins (HDL), as well as decreased activity of lipoprotein-lipase (LPL), is observed. Also, activity of hepatic triglyceride-lipase is decreased both in experimental animals and humans (see Metabolism, 37:859–865, 1988). Hyperlipidemia results from accumulation of VLDL and LDL in plasma and delayed clearance of these lipoproteins, or increased synthesis of lipoproteins.

Lipoproteins are directly involved in host response to infection, and endotoxin-induced hyperlipidemia represents a physiological defence mechanism. Endotoxin interacts with cholesterol-ester rich lipoproteins. HDL have been shown to bind endotoxin (see J. Clin. Invest., 67:827–837, 1981). After binding to HDL, the ability of endotoxin to induce fever, leucocytosis and hypotension is dramatically reduced (see J. Clin. Invest., 62:1313–1324, 1978). In rabbits LDL can also bind endotoxin in the same way and LDL-bound endotoxin shows less toxicity. It has also been shown (see J. Clin. Invest., 86:696–702, 1990) that VLDL, chylomicrons and artificial lipid emulsions can protect mice against endotoxin-induced death. Furthermore, triglyceride-rich lipoproteins inactivate endotoxin in vitro. Triglyceride-rich lipid solutions and chylomicrons have been shown to significantly improve survival in animals with sepsis and reduce the serum level of endotoxin and TNF (see J. Clin. Invest., 91:1028–1034, 1993).

As noted above, the entry step for many antigens, such as bacteria, into cells is determined by membrane-related processes, such as endocytosis. These processes include changes in membrane shape and conformation, and thus may be affected by physico-chemical factors.

There are several known approaches that disrupt receptor-mediated endocytosis or non-receptor mediated endocytosis and phagocytosis, and membrane trafficking. They involve depletion of calcium or other ions, application of cytochalasin or related substances to prevent actin polymerization in cells, and inhibition of the cell energy production by toxins. However, all these approaches are not applicable for the purposes of treatment of a whole living organism to combat topical bacterial infection.

In treatment of sepsis, application of specific antibodies to particular receptors or antigens was not shown to be beneficial in clinical practice. Usually the exact type of antigen in disease is not known. The immense variety of antigens makes the attempts to use specific antibodies impractical in wide medical practice. Also, immunotherapy in these cases is extremely expensive. Other approaches to inactivate endotoxins and to treat septic shock include the use of peroxy-diphosphate compounds (U.S. Pat. No. 5,034,383), steroids (U.S. Pat. No. 4,844,894) and lipid analogues-sphingosine (U.S. SIR No. H1,168).

Previous studies have shown that detergents are strong modulators of membrane-related processes (see Attwood D. & Florence A., Surfactant Systems (1983)). It is well known that detergents and related pharmaceutical drugs at appropriate concentrations stabilize biological membranes and attenuate, for example, erythrocyte osmotic lysis. Detergents are also reported to be successfully used in treating vascular and is chemic disorders (U.S. Pat. Nos. 5,152,979, 5,240, 702, 5,080,894, 5,078,995, 5,089,260 and 5,182,106).

Detergents of different origin are important components of all body liquids. Interaction between detergents, lipids and proteins determines cell membranes fluidity, permeability and activity of membrane enzymes. Proteins themselves are evidently the most important and potent surfactants of the body. Bile salts are also important native surfactants, as well as corticosteroids, polypeptides and lipoproteins.

Phagocytosis of bacteria by neutrophils is dependant upon the adhesiveness of bacteria and neutrophils, which is surface related phenomena (see van Oss, C. J. et al., Phagocytic Engulfment and Cell Adhesiveness (1975)). Studies have shown that application of detergents sodium deoxycholate and Tween 80 at 0.01% to the cell media reduced phagocytosis of Staphylococcus epidermis by human neutrophils by four-fold. Detergents oppose endocytosis and promote exocytosis. Antibiotics of the polymyxin group, which are polycationic detergents of a polypeptide nature, interfere with the bacterial membranes, causing appearance of numerous profusions or blebs, extending from the outside surface of the cell. The same processes were also observed in non-bacterial cells (see Storm, D. L. et al., Polymyxin and related peptide antibiotics, Ann. Rev. Biochem., 46:723–763 (1977).

In addition, in vitro studies have shown that synthetic phosphatidylcholine stopped vesiculation in platelets, and at an appropriate concentration induced the opposite process—formation of cell podii and zeiosis (see J. Pharmacobio-Dynamics, 9:131–137, 1986). Endocytosis of horseradish peroxidase in smooth muscle and endothelial cell cultures was inhibited in dose and time dependant manner by cholestane and hydroxycholesterol (see Artery, 17:84–95, 1990). In vitro adherence and migration of granulocytes were inhibited by Pluronic F68. The same effect was also demonstrated in vivo (see Proc. Soc. Exp. Biol. Med., 188:461–470, 1988).

Detergents can provide a direct lytic action on bacterial cells in vitro. Detergents are also known to induce hyperlipidemia. Tyloxapol (e.g., Triton® WR-1339) is the most widely used detergent to induce hyperlipidemia in animal models (see J. Exp. Med., 114:279–293, 1961). Lipidemia and increase in plasma LDL has been reported after infusion of Triton® A-25, Polysorbate-80, Pluronic and Cremophor EL (see Attwood, et al., 1980). The mechanisms involved are blockade of lipoprotein-lipase and LDL receptors, and formation of "micelies" with lipoproteins.

As described above, plasma lipoproteins possess a marked anti-endotoxin effect, and detergents have a regulatory effect on membrane-related transfer processes in cells. However, the use of biologically active detergents for modification of lipid metabolism and plasma levels of lipoproteins and membrane traffic modification for the treatment of endotoxemia and sepsis has not been previously disclosed.

Accordingly, it is an object of the present invention to provide such a method, useful in the treatment of bacterial infection and associated toxemia, based on the physicochemical properties of non-ionic detergents.

SUMMARY OF THE INVENTION

The present invention is directed to a method for treating toxemia insepsis or topical bacterial infection comprising administration of biologically active non-ionic detergents. Biologically active detergents can act by several mechanisms: a) directly inactivate toxins in biological fluids and bloodstream; b) block the uptake of lipoproteins by the blockade of enzyme lipoproteinlipase which subsequently increases the plasma level of lipoproteins, the later being scavengers of toxins; c) block the uptake of the toxins by macrophages, monocytes and other cells which in turn prevent them from releasing the bioactive cellular mediators of septic shock. Administration of biologically active detergents in models of sepsis and endotoxemia results in abolition of release of biologically active compounds like TNF, prevents the development of septic shock and increases the survival in sepsis several-fold.

BRIEF DESCRIPTION OF THE DRAWING

The Figure is a graph of the relative concentration of labelled lipopolysaccharide in the perfusate of perfused dogs lungs versus time.

DETAILED DESCRIPTION OF THE INVENTION

Exogenous biologically active non-ionic detergents of different origin, and detergent-like pharmaceutical agents are capable of modification of membrane-related cell activity and host response to invasion of toxins, including bacteria and other antigens. Penetration of these agents occurs via endocytotic vesicular transport. Though, in receptor-mediated endocytosis, active cytoskeleton involvement reduces the role of cellular membrane conformation change, it still remains an important step in the transfer process. In non-receptor mediated endocytosis vesicle formation is thought to be induced by adsorption of substances on the cell surface. Microvesicular transport in endothelium, or transcytosis, is mostly non-receptor mediated and does not involve any cytoskeleton activity.

The main triggering mechanism for the formation of vesicles in non-receptor mediated endocytosis is a non-uniform distribution of the free surface energy across the plane of a cell membrane. This non-uniformity is provided by cluster-like structures on biological membranes and non-uniform adsorption of various substances on membranes. Local absorption of a substance changes the free surface energy of a membrane locally and produces bending which culminates in vesicle formation. The adsorbed material, that triggered the formation of a vesicle, is thus coated by a surface membrane and transferred across the cell.

Application of detergent substantially reduces the inhomogeneity of free surface energy on the cell membrane. This physico-chemical effect will lead to less advantageous conditions for formation of vesicles, or even may completely abolish vesiculation.

In carrying out the method of the invention, the desired detergent may be introduced into systemic circulation by any convenient means. Preferably the detergent is introduced parenterally. Detergent may be administered by injection, intravenously, intramuscularly, intratracheally, into the body cavity (intraperitoneally or intrapleurally) or subcutaneously. Other methods of administration may also be adopted, as an inhaled aerosol spray, oral administration or rectal administration in the form of suppository.

A pharmaceutical composition comprising an effective amount of an appropriate detergent should be adapted to administration by a route capable of producing an elevated concentration of detergent in systemic circulation. Preferred forms of a pharmaceutical composition according to the invention comprise injectable solutions or suspensions of detergents, aerosol sprays, suppositories, or dosage forms adopted for oral administration. The compositions may comprise conventional pharmaceutically acceptable diluents or carriers. Typical injectable solutions will comprise sterile pyrogen-free media, e.g. normal saline, and optionally include buffering agents, stabilizing agents and preservatives.

Solutions which may be typically employed in the preparation of the detergent composition include, but are not limited to, phosphate buffered saline, normal saline, Ringers solution, lactated Ringers solution, Krebs-Ringers solution, various sugar solutions. These solutions are well known to one of ordinary skill in art. Also, detergents may be administered as a solution that is not isotonic. Preferably, the composition should be adjusted to normal blood pH by any convenient buffer. Detergents may also be administered in non-aqueous solution, lipid emulsions or microemulsions. Solutions of the detergent should be prepared within the concentration range of a detergent of 10–500 mg/ml, preferably within the range 25–150 mg/ml.

The effective concentration of detergent in blood or other biological fluids used to practice the present invention is between approximately 0.01 and 25 mg/ml. The preferred concentration used to practice the present invention is between approximately 0.2 to 1.2 mg/ml or approximately 50 µM (depending on the molecular weight of the detergent).

To maintain an effective plasma concentration of the detergent in the systemic circulation (0.2–1.2 mg/ml, or 10–100 µM, depending on the average molecular weight of detergent), it is preferable to administer detergent intravenously as a bolus, slow drip or both in a manner so as to maintain a steady venous pressure. After the initial bolus injection, continuous infusion of the detergent solution is preferable.

The blood concentration of the detergent should be approximately between 0.1 mg/ml to 25 mg/ml, preferably between 0.2 and 1.2 mg/ml. The concentration of detergent is maintained between approximately 0.2 to 1.2 mg/ml of blood for between approximately 4 hours to 120 hours.

The detergent is administered in divided doses, e.g. doses from 10 to 200 mg/kg body weight per day. A particularly preferred dosage of detergent contains about 100 mg/kg of detergent.

Detergents useful in the practice of the present invention include polymerized oxyethylene ethers, including polyoxyethylated alkylphenols. Particularly preferred detergents of this class are Triton® X-100 (Union Carbide Chemicals and Plastics Co., Inc. (Union Carbide)) having the following chemical structure:

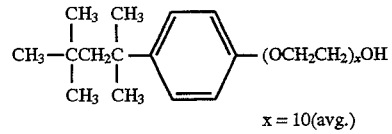

x = 10(avg.)

and Tyloxapol.

Triton® X-100 is a proprietary compound of Union Carbide widely available and commonly used as a biological detergent. Tyloxapol is available from a variety of sources, for example, from Union Carbide as Triton® WR-1339, a 4-(1,1,3,3,-Tetramethylbutyl)phenol polymer with formaldehyde and oxirane.

Other detergents which may be useful in the practice of the invention include acetylenic surfactants, alcohol ethoxylates, amine oxides, alkyl polyglycosides, ethoxylated alkanolamides, ethoxylated amines, ethylene oxide/propylene oxide co-polymers, fatty acid ethoxylates, sorbitan esters, sorbitan ester ethoxylates, and glycol/glycerol esters and ester ethoxylates.

Infusion of detergent may be performed as a prophylaxis or a treatment procedure. The schedule of the treatment by the detergent depends on the specific terms of the disease evolution.

The mechanism of detergent action described above disrupts the entry of toxins, bacteria, viruses and other antigens into cells. The same mechanism is responsible for the attenuation of phagocytosis of endotoxin by macrophages and monocytes, which is the key step in development of septic shock through the release of cytokines.

The biologically active detergents also inactivate bacteria upon contact. This property is used in bactericidal compositions, applied topically (see, e.g., U.S. Pat. No. 5,182,104). Bacteria contain lipids in their membranes which are subject to direct action of detergents. Endotoxins of Gram-negative bacteria contain a lipid part which is also subject to direct detergent action. Various detergents have been shown to provide a direct detoxifying effect on endotoxins in vitro (see J. Bacteriol., 96:1611–1616, 1968).

The other important mechanism of detergent action is blockage of lipoprotein-lipase, which increases the level of plasma lipoproteins and triglycerides. As noted above, lipoproteins play an important role in scavenging the endotoxin in sepsis. Non-ionic detergents are capable of enhancing the action of plasma lipoproteins in vivo. Detergents increase the concentration of lipoproteins, which in turn free organism from active circulating endotoxin. This action of detergents is sufficient for the substantial reduction in lethality due to endotoxemic shock.

In the view of these considerations non-ionic detergents may be used for the treatment of sepsis and associated endotoxemia.

Non-ionic detergents are used presently used systemically for many purposes, for instance treating vascular obstructions (U.S. Pat. No. 5,152,979), treating stroke (U.S. Pat. No. 5,240,702), reducing tissue damage (U.S. Pat. No. 5,080,894), fibrinolysis (U.S. Pat. No. 5,078,995), treating ischemic tissue (U.S. Pat. No. 5,089,260), stimulating the immune system (U.S. Pat. No. 5,234,683), and treating hypothermia (U.S. Pat. No. 5,182,106) at concentrations which provide direct effect on bacteria, viruses and toxins. However, the application of these agents to the treatment of toxemia has not been suggested.

From the above discussion it will be appreciated that the present invention provides a method for systemic therapeutic and prophylactic treatment of toxemia associated with bacterial infections, including sepsis. The following examples are illustrative of the action of the detergent compositions of the method of the present invention.

EXAMPLE I

The goal of this study was to investigate the influence of detergent from the group of polyoxyethylated alkylphenols on the uptake of endotoxin by monocyte-macrophage system and development of organ alterations produced by endotoxin.

The study was performed in 16 perfused in situ dog lungs prepared in the following manner. Mongrel dogs of either sex 16–22 kg in weight were anesthetized with 10–20 mg/kg body weight thiopental sodium, given intravenously. Animals were placed in the supine position, intubated and ventilated by a volume respirator with 6–10 cm $H_2O$ end inspiratory pressure and zero expiratory pressure. The right lymphatic duct was cannulated with polyethylene tubing using the procedure described by Gee et al. (Microvasc. Res. 1980, 19, 209–216). A catheter was placed into the femoral artery, and after heparin (1000 U/kg body weight) intravenous (i.v.) administration the animals were killed by exsanguination.

Through the fifth left interspace incision the pulmonary artery and left atrium were cannulated. The aorta, vena cava superior and inferior, and hemiazygos vein were ligated. The lungs were connected to an extracorporeal circuit and perfused by roller pump with autologous blood at a temperature of 38° C. Perfusate flow was measured with electromagnetic flow probe (Nihon Cohden, MFP-1200, Japan). Pressures in the pulmonary artery and left atrium were measured by EMT-34 pressure transducers (Mingograf-34,Siemens, Sweden).

The lungs were ventilated at tidal volume of 0.86 liter and a frequency 5 breaths/minute. Perfusate oxygen ($O_2$) and carbon dioxide ($CO_2$) tensions, and pH level were controlled by standard electrode techniques (BMS-3, Radio-meter, Sweden). pH was maintained by adding gaseous carbon dioxide to the inspired air. Lymph flow rate via the right lymphatic duct was measured by a calibrated micropipette. Changes of perfusate volume in the reservoir were used to estimate the changes of lung extravascular volume according to the method given by Mitzner et al. (J. Appl. Physiol. 61, 1830–1835, 1986).

To study the permeability of lung endothelium to a middle-molecular weight tracer we used the uptake of dichlor-fluorescein (0.05% solution in ethanol), which was introduced into the perfusate at the dose 0.005 mg/ml. Concentration was measured by spectrofluorimeter.

To study the uptake by macrophages and endothelial cells of the lungs lipopolysaccharide E. coli, labeled with tritium (96% chromatographically pure, gift of Radium Institution named after G. Hlopin, St. Petersburg, Russia) was used a marker of endotoxin uptake by the macrophage-monocyte system of the lungs. The concentration of label was also measured in lymph from the lungs. Activity of tritium was measured in beta-counts in PRO-POPOP scintillation liquid. Also, the concentration of lactate-dehydrogenase was measured in perfusate as a marker of cellular injury by automated analyzer. The condition of endothelium and number of vesicles after four hours of perfusion was investigated by electron microscopy after intrabronchial fixation with glutaric aldehyde.

To produce endotoxin injury, rough endotoxin from E. coli, strain B5, at a dose 13 mg/kg (gift from the Laboratory of Applied Immunology, Kirov Medical Institute, St. Petersburg, Russia) was used. Toxicity of the endotoxin was estimated in mice ($LD_{50}$=13 mg/kg for mice).

Control samples (n=6), without addition of any substances to the perfusate, were compared with experimental (n=10), where either endotoxin alone (n=5), or endotoxin and non-inogenic surfactant Triton X-100 (n=5) were both added to the perfusate to achieve a detergent concentration of 50 µM.

The Figure shows the uptake of labeled endotoxin by the lung macrophage-mononuclear system from the perfusate. The uptake of labeled lipopolysaccharide by the lung vasculature was over 20% in control studies over a one hour period. In endotoxin injury the uptake of labeled endotoxin increased to 30%. Uptake of endotoxin was completely abolished during one hour after Triton X-100 was added to the perfusate. Appearance of lipopolysaccharide in the lung lymph was facilitated compared to control in endotoxin injury but it was reduced by 85% in Triton studies. These results show, that administration of Triton X-100 blocks the uptake of endotoxin by microphage-monocyte system.

Table 1 shows the results of filtration rates, permeability of the lungs to dichlorfluorescein and concentration of the lactate-dehydrogenase in control, endotoxin and detergent studies after four hours. Data are given as MEAN±SD, *-$p<0.05$ between control and Endotoxin groups, +- $p<0.05$ between Endotoxin, and Detergent plus Endotoxin groups.

| Variable | Control | Endotoxin | Detergent + Endotoxin |
|---|---|---|---|
| Filtration rate ml/min | 1.3 ± 0.4 | 2.5 ± 1.20* | 0.96 ± 0.51+ |
| Permeability to dichlor-fluorescein (cm/min × $10^{-5}$) | 1.12 ± 23 | 2.8 ± 0.98* | 1.40 ± 0.33+ |
| LDH (Units/l) | 220 ± 22 | 752 ± 95* | 170 ± 33+ |

As is readily seen from the table, permeability to water (filtration rate), middle-molecular weight tracer and concentration of intracellular enzyme were significantly increased in endotoxin injury. However, detergent from the group of polyoxyethylated alkylphenols, e.g., Triton X-100, prevented the development of endotoxin injury. Also, electron microscopic studies showed considerably better status of the pulmonary endothelium after four hours of the perfusion in the experimental seria (less endothelial desquamation, swelling and better membrane integrity). The remarkable finding was fewer luminal endothelial vesicles (almost 3 fold per endothelial cell volume) in detergent seria compared to control.

The results of this experiment show that detergent Triton X-100 at 50 µM substantially decreases the vesiculation of pulmonary endothelium. No hemolysis was noticed after Triton X-100 administration. The detergent thus is capable of protecting an isolated perfused organ from endotoxin injury.

EXAMPLE II

To study the in vivo effect of detergent on endotoxemia, a model study was performed in 15 dogs. Mongrel dogs of either sex 16–22 kg in weight were anesthetized with 10–20.mg/kg body weight thiopental sodium, given intravenously. Animals were placed in the supine position, intubated and ventilated by a volume respirator with 6–10 cm $H_2O$ end inspiratory pressure and zero expiratory pressure. Catheters were placed into the femoral artery and vein. Systemic arterial and venous pressure, electrocardiogram (ECG) and blood gases were monitored for a period of up to 10 hours.

In the control group, dogs received infusion of 0.25 liter of normal saline intravenously over 30 minutes. In the experimental group (n=6), animals were given E. coli endotoxin. Rough endotoxin from E. coli, strain B5, at a dose 13 mg/kgo (gift from the Laboratory of Applied Immunology, Kirov Medical Institute, St. Petersburg, Russia) was used. Endotoxin was infused intravenously, in a solution of 250 ml of normal saline over 30 minutes. In the detergent group, infusion of 100 mg/kg Triton X-100 in normal saline (10 mg/ml) was given prior to the infusion of the same dose of endotoxin.

None of the control animals died. In the endotoxin group, four animals (66%) died within the first four hours of infusion from systemic shock. None of the detergent-treated animals died.

The time course of the systemic arterial pressure for all three groups is given in Table 2. Data are given as MEAN±SD, *-$p<0.05$ between control and Endotoxin groups, +$p<0.05$ between Endotoxin and Detergent plus Endotoxin groups.

| Systemic arterial pressure, cPa | Control | Endotoxin | Detergent + Endotoxin |
| --- | --- | --- | --- |
| Baseline | 15.9 ± 2.1 | 14.5 ± 2.20 | 15.2 ± 3.62 |
| 30 min after infusion | 14.5 ± 3.1 | 6.8 ± 2.98* | 14.10 ± 3.2+ |
| 2 hours after infusion | 13.2 ± 3.5 | 5.8 ± 1.30* | 11.5 ± 2.1+ |
| 4 hours after infusion | 13.1 ± 2.8 | 5.1 ± 0.95* | 12.1 ± 2.4+ |

As is readily seen from the table, animals in the endotoxin group experienced a rapid decrease in systemic arterial pressure, indicative of systemic shock. This was accompanied by metabolic acidosis. Detergent treated animals did not develop shock. Thus, infusion of detergent in vivo protects against endotoxin-induced shock and death.

EXAMPLE III

The protective effect of non-ionic polyoxyethylene ethers for the treatment of sepsis was studied in rats. In the first study, 24 rats were anesthetized with ether inhalation and cecal ligation and puncture was performed to produce a model of intraabdominal sepsis and endotoxemia according to the method in J. Clin. Invest. 88:34–39, 1991. The abdomen was sterilely opened via middle-line incision, the caecum was identified, and ligation of caecum was performed at the level of ileum. Two punctures of the avascular portion of the gut were done, then caecum was put back into the abdomen. The abdomen was closed in layers. Twelve of these animals received 250 mg/kg of Tyloxapol intravenously in 2.5 ml of phosphate-buffered saline immediately with cecal puncture. The control group received only vehicle. Survival was determined up to 120 hours after cecal ligation and puncture.

In the control group (vehicle only), survival over the first 48, 96 and 120 hours was 52%, 21% and 9% respectively. In the Tyloxapol-infused animals, survival was 95%, 86% and 78% respectively at the same time intervals. As these results demonstrate, Tyloxapol significantly increased survival of septic animals.

The present invention has been illustrated by means of several examples. The invention, however, is not limited to the embodiments depicted and described in the examples. The invention may be embodied in other specific forms without departing from its spirit or essential characteristics. The examples are intended only as illustrative and not restrictive. Rather, the scope of the invention is defined by the appended claims.

What is claimed is:

1. A method for treating toxemia in an individual comprising administering a pharmaceutical composition comprising an effective amount of Tyloxapol sufficient to block the action of lipoprotein-lipase and to disrupt endocytosis and phagocytosis of toxins in body cells.

2. A method according to claim 1, wherein said effective amount is in the range of about 10 to 200 mg/kg of body weight per day.

* * * * *